(12) United States Patent
Weadock et al.

(10) Patent No.: US 8,894,683 B2
(45) Date of Patent: Nov. 25, 2014

(54) DEVICE FOR ATTACHING, RELOCATING AND REINFORCING TISSUE AND METHODS OF USING SAME

(75) Inventors: Kevin S. Weadock, Hillsborough, NJ (US); Parris Wellman, Hillsborough, NJ (US); Martin Weisberg, Elkins Park, PA (US); Philip Prentice, Annandale, NJ (US); Earl Adamy, Clinton, NJ (US)

(73) Assignee: Ethicon, Inc., Somerville, NJ (US)

( * ) Notice: Subject to any disclaimer, the term of this patent is extended or adjusted under 35 U.S.C. 154(b) by 1459 days.

(21) Appl. No.: 12/151,235

(22) Filed: May 5, 2008

(65) Prior Publication Data

US 2008/0208251 A1    Aug. 28, 2008

Related U.S. Application Data

(62) Division of application No. 11/321,688, filed on Dec. 29, 2005, now abandoned.

(51) Int. Cl.
*A61B 17/08* (2006.01)
*A61B 17/00* (2006.01)
*A61B 17/04* (2006.01)
*A61F 2/00* (2006.01)

(52) U.S. Cl.
CPC ... *A61B 17/0401* (2013.01); *A61B 2017/00805* (2013.01); *A61B 2017/0462* (2013.01); *A61B 2017/0454* (2013.01); *A61B 2017/00778* (2013.01); *A61B 2017/00004* (2013.01); *A61B 2017/0412* (2013.01); *A61B 2017/0427* (2013.01); *A61B 2017/0464* (2013.01); *A61B 2017/00743* (2013.01); *A61B 2017/0458* (2013.01); *A61F 2/0045* (2013.01)
USPC ............................ 606/215; 606/216; 606/213

(58) Field of Classification Search
USPC .................................. 606/213, 215–218, 232
See application file for complete search history.

(56) References Cited

U.S. PATENT DOCUMENTS 268,632 A * 12/1882 Danforth ...................... 606/218
583,455 A *  6/1897 Bush ............................. 606/75

(Continued)

FOREIGN PATENT DOCUMENTS

| EP | 0632999 | 1/1995 | ............ A61B 17/04 |
| EP | 0502698 | 11/1997 | ............ A61B 17/86 |

(Continued)

OTHER PUBLICATIONS

Notification of Transmittal of the International Search Report and the Written Opinion of the International Searching Authority, or the Declaration; International Search Report; and Written Opinion of the International Searching Authority.

*Primary Examiner* — Dianne Dornbusch
(74) *Attorney, Agent, or Firm* — Doherty IP Law Group LLC

(57) ABSTRACT

A device for attaching, relocating or reinforcing tissue includes a first tissue anchoring portion having a support plate and a plurality of barbs extending from the support plate for engaging tissue at a first location, a second tissue anchoring portion having a support plate and a plurality of barbs extending from the support plate for engaging tissue at a second location which is different from the first location, and a connection element, such as a suture or a mesh structure, interposed between and interconnecting the first tissue anchoring portion and the second tissue anchoring portion. The support plate of at least one of the first tissue anchoring portion and the second tissue anchoring portion may have longitudinally axially formed therethrough a bore for receiving the connecting element so that the surgeon may pull on the end of the connecting element to adjust the distance between the first tissue anchoring portion and the second tissue anchoring portion.

19 Claims, 6 Drawing Sheets

(56) References Cited

U.S. PATENT DOCUMENTS

| | | | |
|---|---|---|---|
| 3,118,201 A * | 1/1964 | Beghetto, Jr. | 24/16 R |
| 3,385,299 A * | 5/1968 | Le Roy | 606/218 |
| 3,976,079 A * | 8/1976 | Samuels et al. | 606/232 |
| 4,865,026 A * | 9/1989 | Barrett | 606/214 |
| 4,969,892 A * | 11/1990 | Burton et al. | 606/218 |
| 5,067,955 A | 11/1991 | Cotrel | 606/61 |
| 5,261,914 A | 11/1993 | Warren | 606/73 |
| 5,269,809 A * | 12/1993 | Hayhurst et al. | 606/232 |
| 5,275,601 A | 1/1994 | Gogolewski et al. | 606/72 |
| 5,356,412 A * | 10/1994 | Golds et al. | 606/74 |
| D352,356 S * | 11/1994 | Hirshowitz et al. | D24/145 |
| 5,370,661 A * | 12/1994 | Branch | 606/232 |
| 5,391,173 A * | 2/1995 | Wilk | 606/144 |
| 5,417,533 A | 5/1995 | Lasner | 411/426 |
| 5,443,482 A | 8/1995 | Stone et al. | 606/232 |
| 5,571,138 A * | 11/1996 | Blomqvist et al. | 606/218 |
| 5,601,557 A * | 2/1997 | Hayhurst | 606/232 |
| 5,611,814 A | 3/1997 | Lorenc | 606/213 |
| 5,725,556 A * | 3/1998 | Moser et al. | 606/232 |
| 5,800,436 A * | 9/1998 | Lerch | 606/324 |
| 5,928,231 A | 7/1999 | Klein et al. | 606/60 |
| 6,015,410 A | 1/2000 | Tormala et al. | 606/73 |
| 6,022,351 A | 2/2000 | Bremer et al. | 606/324 |
| 6,066,160 A * | 5/2000 | Colvin et al. | 606/232 |
| 6,068,631 A * | 5/2000 | Lerch | 606/301 |
| 6,120,525 A * | 9/2000 | Westcott | 606/216 |
| 6,432,123 B2 * | 8/2002 | Schwartz et al. | 606/232 |
| D462,766 S | 9/2002 | Jacobs et al. | D24/146 |
| 6,471,715 B1 * | 10/2002 | Weiss | 606/216 |
| 6,485,503 B2 * | 11/2002 | Jacobs et al. | 606/215 |
| 6,491,714 B1 * | 12/2002 | Bennett | 606/232 |
| 6,645,226 B1 | 11/2003 | Jacobs et al. | 606/215 |
| 6,656,183 B2 * | 12/2003 | Colleran et al. | 606/232 |
| 6,921,401 B2 * | 7/2005 | Lerch et al. | 606/324 |
| 7,235,090 B2 * | 6/2007 | Buckman et al. | 606/215 |
| 7,455,681 B2 * | 11/2008 | Wilke et al. | 606/216 |
| 7,666,197 B2 * | 2/2010 | Orban, III | 606/153 |
| 2001/0051815 A1 * | 12/2001 | Esplin | 606/232 |
| 2003/0065360 A1 | 4/2003 | Jacobs et al. | 606/216 |
| 2003/0074021 A1 * | 4/2003 | Morriss et al. | 606/215 |
| 2003/0088270 A1 | 5/2003 | Lubbers et al. | 606/213 |
| 2003/0092969 A1 * | 5/2003 | O'Malley et al. | 600/216 |
| 2003/0163160 A1 * | 8/2003 | O'Malley et al. | 606/213 |
| 2004/0111117 A1 * | 6/2004 | Colleran et al. | 606/232 |
| 2004/0147958 A1 * | 7/2004 | Lam et al. | 606/232 |
| 2004/0153075 A1 * | 8/2004 | Roger | 606/72 |
| 2004/0225183 A1 * | 11/2004 | Michlitsch et al. | 600/106 |
| 2004/0267309 A1 | 12/2004 | Garvin | 606/217 |
| 2005/0192629 A1 * | 9/2005 | Saadat et al. | 606/221 |
| 2005/0251206 A1 * | 11/2005 | Maahs et al. | 606/232 |

FOREIGN PATENT DOCUMENTS

| | | | |
|---|---|---|---|
| WO | WO01/67944 | 9/2001 | |
| WO | WO2005/002452 | 1/2005 | A61B 17/08 |

* cited by examiner

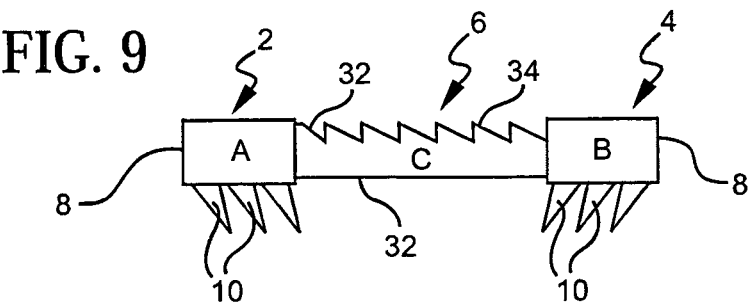
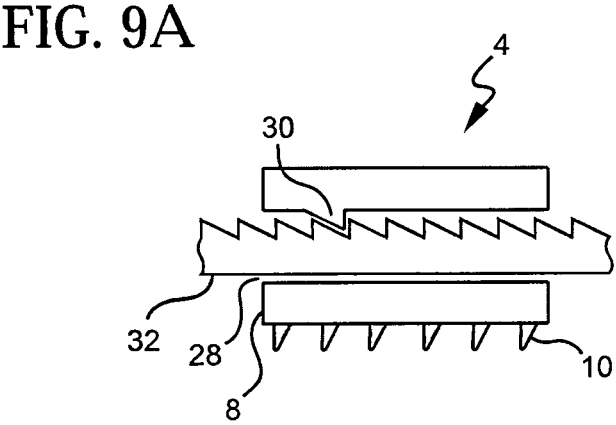
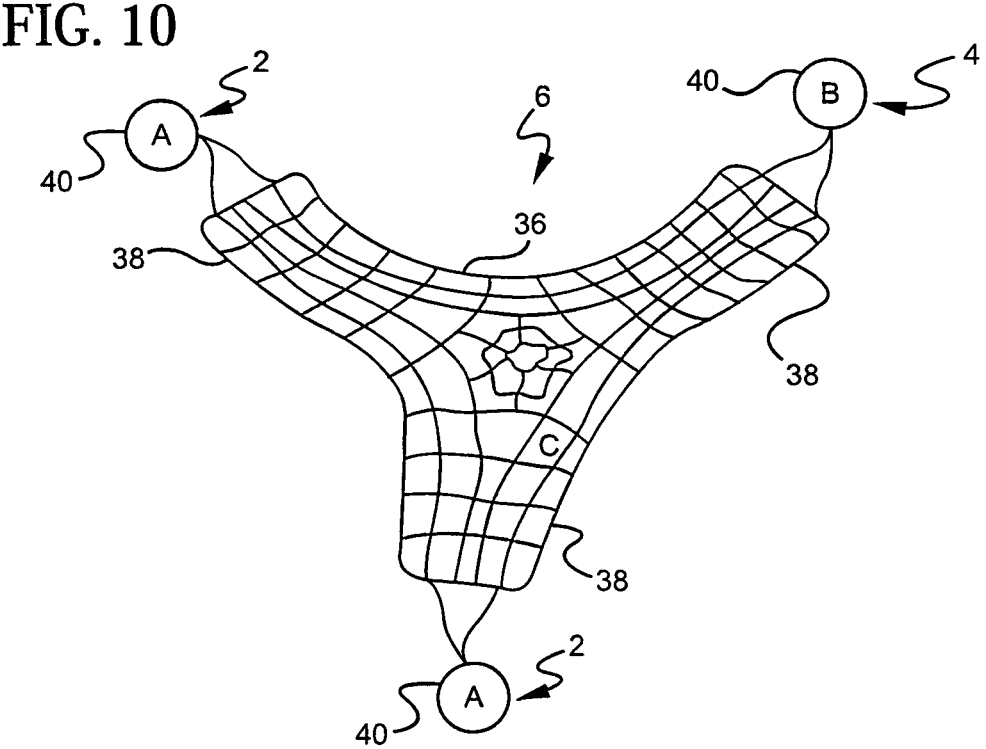

DEVICE FOR ATTACHING, RELOCATING AND REINFORCING TISSUE AND METHODS OF USING SAME

CROSS-REFERENCE TO RELATED APPLICATIONS

This application is a division of co-pending U.S. application Ser. No. 11/321,688, filed on Dec. 29, 2005, and entitled, "Device for Attaching, Relocating and Reinforcing Tissue and Methods of Using Same", the disclosure of which is incorporated herein by reference.

BACKGROUND OF THE INVENTION

1. Field of the Invention

The present invention generally relates to surgical devices for relocating and fixating soft tissue, and more particularly relates to a soft tissue anchoring device for attaching, relocating or reinforcing tissue, such as used in facial plastic surgery.

2. Description of the Prior Art

In many types of surgery, there is a need to suspend soft tissue or relocate the tissue from one position to another. This is often done with sutures, but sutures can pull through the tissue and can be difficult to secure to the tissue by tying knots.

Soft tissue anchors are also well known in the art and are used in different surgical procedures. For example, U.S. Pat. No. 6,645,226, which issued to Daniel Jacobs and Dirk Thye, and U.S. Pat. No. 6,485,503, which issued to Daniel Jacobs and Robert James Elson, the disclosures of which are incorporated herein by reference, disclose one form of a tissue approximation device and method for using the device, wherein the device is an implantable, biodegradable construct that is used to attach one tissue structure to another but requires the presence of natural tissue structures to achieve the desired lift. For example, the aforementioned U.S. Pat. No. 6,645,226 to Jacobs et al. describes a method where the periosteum in a patient's forehead is detached and then relocated by the surgeon. It is then held in place with the implantable tissue anchor disclosed in the patent. The aforementioned U.S. Pat. No. 6,485,503 to Jacobs et al. discloses a similar tissue anchoring device.

The problems with such tissue anchoring devices disclosed in the aforementioned Jacobs et al. patents include the fact that the described tissue anchors cannot be implanted and then adjusted afterwards; the tissue anchors and the adjustment of the anchors to provide the desired lift must be done in a single step. Additionally, the tissue anchors disclosed in the aforementioned Jacobs et al. patents require the surgical creation of a rather large tunnel or elevated flap of tissue in order to relocate the tissue.

OBJECTS AND SUMMARY OF THE INVENTION

It is an object of the present invention to provide a device for attaching, relocating or reinforcing tissue and methods of using such a device.

It is another object of the present invention to provide a device for anchoring to and relocating a variety of tissue types and which is suitable for use in many different body locations and surgical procedures.

It is still another object of the present invention to provide a device which can relocate and fixate tissue in a minimally invasive manner.

It is a further object of the present invention to provide a device which can relocate and fixate tissue and which may be adjusted by the surgeon after being surgically implanted.

It is yet a further object of the present invention to provide a device for anchoring to and relocating tissue which allows the physician to set the tissue engaging structures of the device first and then subsequently adjust the locations of or spacing between the tissue engaging structures.

It is yet another object of the present invention to provide a device for anchoring to and relocating tissue whereby the amount of tissue relocation may be controlled by the surgeon at the time of placement of the device in a patient's body.

It is still a further object of the present invention to provide a device for anchoring to and relocating tissue which may be implanted in a patient's body in open, endoscopic and blind surgical procedures.

It is yet another object of the present invention to provide a device for attaching, relocating or reinforcing tissue and methods for using such a device which overcome the inherent disadvantages of known devices and methods.

In accordance with one form of the present invention, a device for attaching, relocating or reinforcing tissue includes at least two tissue engagement means, including a first tissue engagement means and a second tissue engagement means, and a connection means interposed between and interconnecting the first tissue engagement means and the second tissue engagement means. The first tissue engagement means is located at the site of the tissue to be relocated. The second tissue engagement means is situated at the anchor site. Preferably, the device is adjustable so that the amount of displacement of the tissue may be controlled by the surgeon during the surgical implantation of the device. The first and second tissue engagement means, and the connection means, may be formed from either resorbable or non-resorbable material, and the resorption profile, stiffness, strength and other mechanical and material properties of the device may be tailored to meet the specific needs and objectives of the surgeon.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 9 is a perspective view of a device for attaching, relocating or reinforcing tissue formed in accordance with an eighth form of the present invention.

FIG. 9A is a cross-sectional view of a portion of the device of the present invention shown in FIG. 9.

FIG. 10 is a perspective view of a device for attaching, relocating or reinforcing tissue formed in accordance with a ninth form of the present invention.

DETAILED DESCRIPTION OF THE PREFERRED EMBODIMENTS

Figure 1:
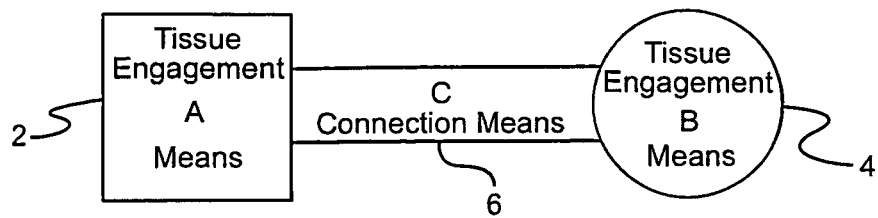
FIG. 1 is a block diagram showing generically the three basic components of a device for attaching, relocating or reinforcing tissue formed in accordance with one form of the present invention.

Referring initially to FIG. 1 of the drawings, it will be seen that, generically, a device for attaching, relocating or reinforcing tissue constructed in accordance with one form of the present invention includes at least two tissue engagement means, and a connection means interposed between and interconnecting the two tissue engagement means. The device of the present invention may include more than two tissue engagement means, such as the three tissue engagement means of the device of the present invention shown in FIG. 10, which will be described in greater detail. The first tissue engagement means 2, which is also designated as "Part A" in FIG. 1, is a tissue anchoring portion of the device that is typically located at the tissue site to be manipulated (e.g., moved). The second tissue engagement means 4, also referred to in FIG. 1 as "Part B", is another tissue anchoring portion of the device that is typically located at the anchor site. The third primary component of the device of the present invention, which is also labeled as "Part C" in FIG. 1, is the connection means 6 which is interposed between and connects the first tissue engagement means 2 and the second tissue engagement means 4. Part C, the connection means 6, could not only be used as an interconnection between the first and second tissue anchoring portions 2, 4, but may also be used to provide tissue support, as will be evident from the detailed description of the various embodiments of the present invention to follow.

Figure 2A:
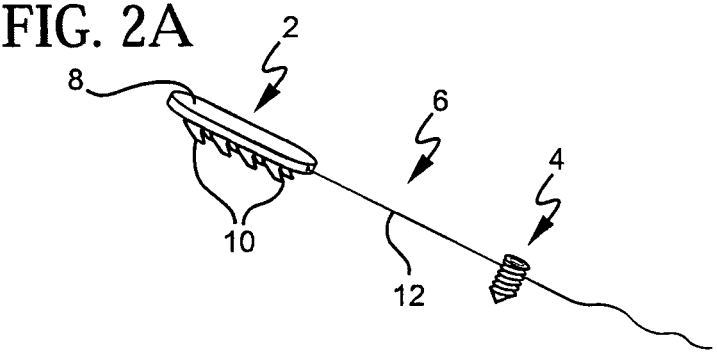
FIG. 2A is a perspective view of a device for attaching, relocating or reinforcing tissue formed in accordance with a second form of the present invention.
Figure 2B:
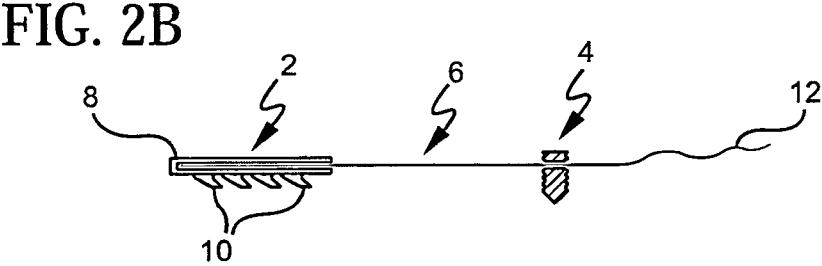
FIG. 2B is a cross-sectional view of the device of the present invention shown in FIG. 2A.
Figure 2C:
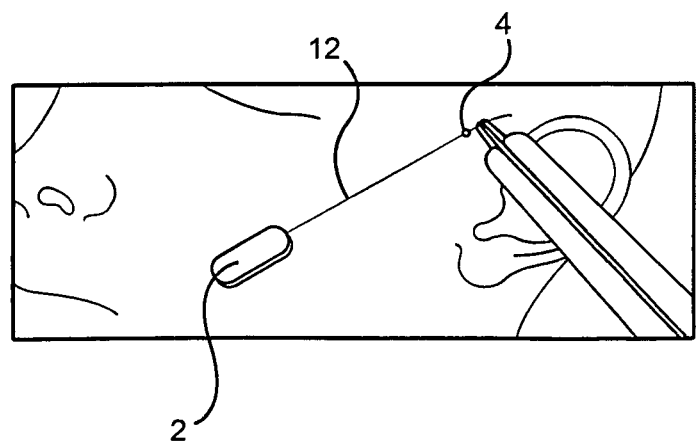
FIG. 2C is a pictorial illustration of the device of the present invention shown in FIGS. 2A and 2B implanted in a patient during facial plastic surgery, and illustrating a method for using the device of the present invention.

One form of the device of the present invention is illustrated by FIGS. 2A-2C. Part A, the tissue anchoring portion 2 which is located at the tissue site to be manipulated, is a barbed, resorbable anchor preferably constructed to include a planar support plate 8 and a plurality of barbs 10 extending outwardly from an exposed surface of the support plate 8 and at an angle thereto, which is preferably between about 30 degrees and about 60 degrees, but is even more preferably at a 45 degree angle, between the barbs and the surface of the support plate 8 from which they extend. One form of material that is resorbable that may be used in the construction of the first tissue engagement means 2, i.e., the "Part A" tissue anchoring portion, is polydioxanone, as an example, but it is envisioned to be within the scope of the present invention to form the "Part A" tissue anchoring portion from other resorbable materials, such as those that will be described later in greater detail.

When anchoring soft tissue to bone or periosteum, the second tissue engager is preferably a bone anchor. Otherwise, they can just be like the first tissue anchor. More specifically, the second tissue engagement means 4, that is, the "Part B" tissue anchoring portion of the device of the present invention, is preferably formed as a bone anchor, such as the Biofastin RC threaded suture anchor manufactured by DePuy Mitek of Norwood, Mass., which has a bore formed through it to allow a suture to pass therethrough. The bone anchor is situated opposite the first tissue anchoring portion 2. A suture 12, preferably made from polypropylene, is the connection means 6, i.e., the "Part C" of the device of the present invention shown generically in FIG. 1, which connects the barbed, resorbable tissue anchoring portion 2 with the Mitek bone anchor 4.

The embodiment of the present invention shown in FIGS. 2A and 2B is particularly suitable for use in relocating the tissues of the midface of a patient by placing the barbed tissue anchoring portion 2 in the malar fat pad, and placing the bone anchor 4 in the skull above the temporal region, as illustrated by FIG. 2C, with the suture 12 extending between and connecting the two tissue anchoring portions 2,4. The surgeon would implant both tissue anchors, and then pull on the suture 12 to adjust the location of the fat pad.

Figure 3A:
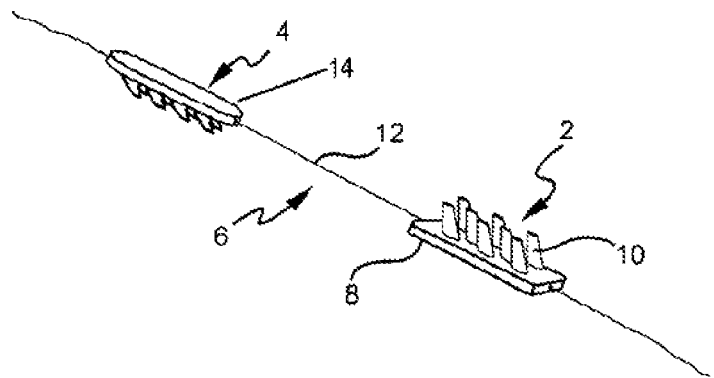
FIG. 3A is a perspective view of a device for attaching, relocating or reinforcing tissue formed in accordance with a third form of the present invention.
Figure 3B:
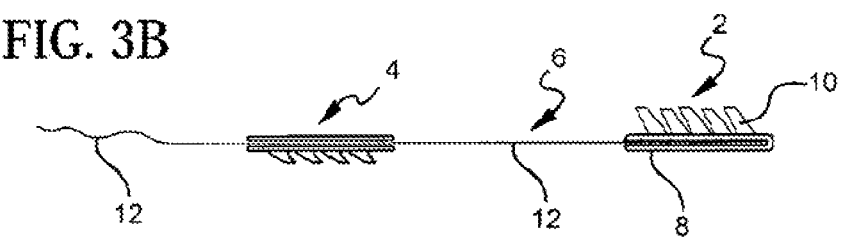
FIG. 3B is a cross-sectional view of the device of the present invention shown in FIG. 3A.
Figure 3C:
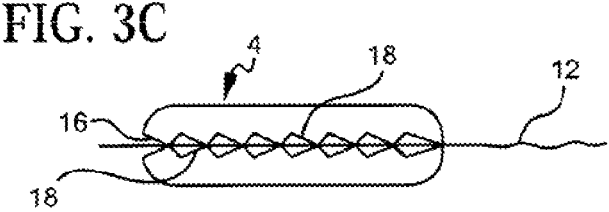
FIG. 3C is a cross-sectional view of a portion of the device of the present invention shown in FIGS. 3A and 3B.

A third form of a device for relocating tissue, constructed in accordance with the present invention, is shown in FIGS. 3A-3C. Here, two preferably permanent (i.e., non-resorbable) first and second tissue anchoring portions 2, 4 (i.e., "Part A" and "Part B" shown in FIG. 1) are joined together with a permanent suture 12 preferably made from polypropylene (i.e., the "Part C" connection means). The "Part A" soft tissue anchoring portion 2 includes a support plate 8 having an exposed surface from which angularly and outwardly extend relatively large barbs 10 (i.e., relative to the "Part B" strong tissue anchoring portion 4). The barbs 10 extend from the surface of the support plate 8 at preferably an angle of between about 30 degrees and 60 degrees, and more preferably, 45 degrees, in the direction of the Part B strong tissue anchoring portion 4. The soft tissue anchor 2 is fixedly joined to the polypropylene suture 12.

The strong tissue anchoring portion (i.e., the "Part B" tissue engagement means 4) may be in the form of a smaller support plate 14 than that of the soft tissue anchoring portion 2 longitudinally through which is formed an axial bore 16. Through the axial bore 16 passes the suture 12. Preferably, the axial bore 16 allows the suture 12 to move therethrough in one direction only, that is, away from the soft tissue anchoring portion 2. Structure to permit uni-directional movement of the suture 12 through the strong tissue anchoring portion 4 may include, for example, ratchet teeth 18 extending from diametrically opposite sides of the bore 16 and radially into the bore to closely engage the suture 12, as shown in FIG. 3C. The ratchet teeth 18 of one side are in mirrored symmetry to the ratchet teeth 18 of the other, and both are angled inwardly of the bore 16 and away from the soft tissue anchoring portion 2. With such structure, the suture 12 may slip past the ratchet teeth 18 in one direction only, that is, away from the soft tissue anchoring portion 2, and the ratchet teeth 18 will exert a force or grip on the suture 12 to prevent its movement in the opposite direction (i.e., toward the soft tissue anchoring portion 2).

The support plate 8 of the soft tissue anchoring portion 2 also includes an exposed surface from which extend a plurality of barbs 10 which are angled from the surface from which they extend at, again, preferably between about 30 degrees and about 60 degrees, and more preferably about 45 degrees. Also, depending on the surgical application, the barbs 10 of the strong tissue anchoring portion 4 extend in a direction opposite to that of the barbs 10 of the soft tissue anchoring portion 2. Furthermore, the barbs 10 of the strong tissue anchoring portion 4 are preferably smaller than those of the soft tissue anchoring portion 2.

The soft tissue anchoring portion 2, with the relatively large barbs 10, is designed for location in the soft tissues of the face and provides good "pullout" strength in fat, while the strong tissue anchoring portion 4, with its relatively smaller barbs 10, is designed to be anchored in stronger tissues, such as the temporalis fascia, or beneath the periosteum. Either one or both of the soft tissue anchoring portion 2 and the strong tissue anchoring portion 4 may be made from a resorbable material.

The anchoring portions 2, 4 of the embodiment of the present invention shown in FIGS. 3A-3C may be surgically implanted in either an open, endoscopic or blind procedure. In the preferred procedure, the surgeon would use a trans-buccal approach under direct visualization to place the soft tissue anchoring portion 2 in the malar fat pad. More specifically, a hollow needle would be blindly inserted through the subcutaneous cheek tissue and up into the temple of the temporalis fascia through a small incision under direct visualization. The suture 12 would then be adjusted until the fat pad is in the desired and appropriate position, and then it would be tied off. Alternatively, the temporalis fascia anchoring portion 4 could incorporate a suture gripping means, such as the ratchet teeth 18 described previously, so that the suture 12 would not require a knot. Although the ratchet teeth 18 was described as one form of suture gripping means, it is envisioned that other means could be employed, including a pre-tied knot, a friction locking collar, a crimped-on staple or any other means known to secure a suture, filament, line, string or rope, for example, to a cleat, clamp or other securing device.

Figure 4:
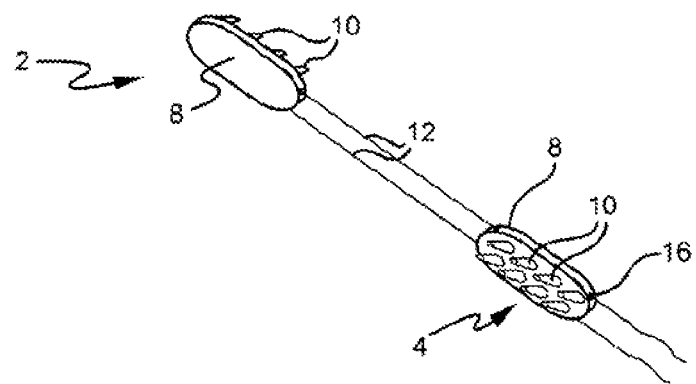
FIG. 4 is a perspective view of a device for attaching, relocating or reinforcing tissue formed in accordance with a fourth form of the present invention.
Figure 5:
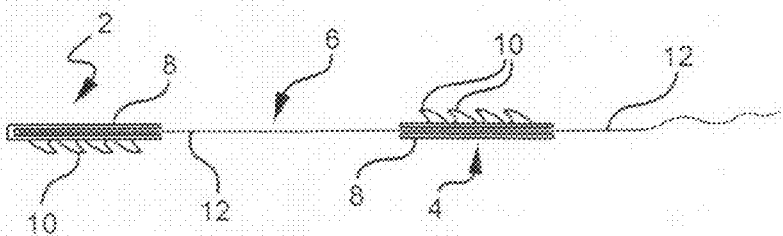
FIG. 5 is a cross-sectional view of the device of the present invention shown in FIG. 4A.

A fourth embodiment of a tissue anchoring, relocating or reinforcing device formed in accordance with the present invention is shown in FIGS. 4 and 5. The "Part B" tissue engagement means 4, i.e., a tissue anchoring portion that is located at the anchoring site, includes a support plate 8 having an exposed surface from which outwardly extends a plurality of angled barbs 10. The barbs 10 are preferably angled to the same degree as previously described with respect to the other embodiments of the present invention. A single bore or two separate parallel bores 16 extend longitudinally axially through the thickness of the support plate 8. A pair of sutures 12 are received by and pass through the single or separate parallel bores 16. This support plate 8 may include suture gripping means, such as the ratchet teeth 18 previously described, or a friction locking collar, crimped-on staple or other means to provide one-way movement of the suture 12 through the support plate of the tissue anchoring portion.

A "Part A" tissue anchoring portion 2, i.e., the one that is located at the site to be manipulated, is also included. This anchoring portion 2 includes a support plate 8 having an exposed surface from which outwardly extends a plurality of angled barbs 10. Again, the barbs 10 extend preferably at the same preferred angle as the barbs 10 previously described with respect to the other embodiments of the present invention. Also, the barbs 10 extend from the support plate 8 of the "Part A" tissue anchoring portion 2 in a direction which is opposite to that of the barbs 10 of the "Part B" tissue anchoring portion 4. Also, depending on the particular surgical procedure and application of the device, the barbs 10 of this anchoring portion 2 may extend from a side of the support plate 8 which is in an opposite facing direction to the side of the support plate 8 of the other anchoring portion 4 from which the barbs 10 extend. The two sutures 12 are fixedly joined to the support plate 8 of this tissue anchoring portion 2.

The "Part A" tissue anchoring portion 2 is designed to grip strong tissues, such as ligaments and other connective tissue, tendons, muscle fascia and periosteal fascia, and the "Part B" tissue anchoring portion 4 is designed to be anchored in other strong tissues, such as beneath the temporalis fascia. The two anchoring portions 2,4 are connected by the sutures 12. In a test procedure that demonstrated the suitability of the fourth embodiment of the present invention for facial plastic surgery, the "Part A" anchoring portion 2 was placed in a cadaver's maxillo-buccal ligament through an open approach. A small incision was made above the left ear of the cadaver, and forceps were inserted blindly subcutaneously through the cheek tissue of the patient; then, the sutures 12 were brought through the cheek tissue. The "Part B" anchoring portion 4 was inserted through a small open incision placed beneath the temporalis fascia, and the first anchoring portion 2 was then adjusted by pulling the sutures 12 and tying them off. The location and dissection path of the anchoring device of the present invention are shown in FIG. 5 of the drawings. It should be noted that the open dissection of the cheek tissue was only performed for experimental purposes. The preferred method of placement of the device is through an endoscopic tunnel that begins at the temporal incision.

It is envisioned as part of the present invention to form the first tissue engagement means 2, i.e., the "Part A" tissue anchoring portion, and the connection means 6, the "Part C" component, or the second tissue engagement means 4, i.e., the "Part B" tissue anchoring portion, and the "Part C" connection means 6, as a single unitary piece. For example, if the connection means 6 and the second tissue engagement means 4 were formed from a mesh material, and the connection means 6 and/or the first tissue engagement means 2 were adjustable in distance from the second tissue engagement means 4, then such a device may be suitable for use as a malar fat pad relocation device. Such a device formed in this manner is shown schematically in FIG. 6.

Figure 6:
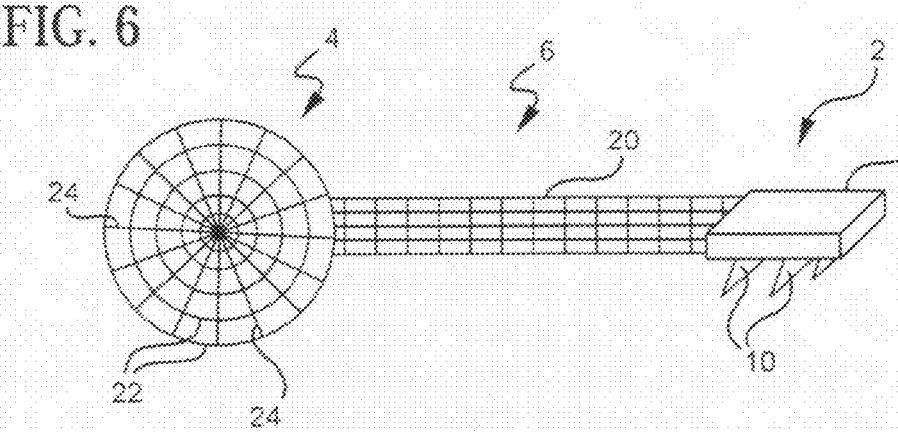
FIG. 6 is a perspective view of a device for attaching, relocating or reinforcing tissue formed in accordance with a fifth form of the present invention.

More specifically, FIG. 6 shows an elongated connection means formed as a strip 20 of mesh material which is connected to the second tissue engagement means 4 (i.e., the "Part B" tissue anchoring portion), which is also formed from a mesh material. The second tissue anchoring portion 4 is shown in a "spider web" configuration, that is, generally round with concentrically disposed circular strands 22 joined to radially extending strands 24. Of course, it is envisioned to be within the scope of the present invention to form the "Part B" tissue anchoring portion 4 in other shapes and configurations from that which is shown in FIG. 6 and described previously. The elongated mesh connection means 20 is attached to a "Part A" tissue engagement means 2, or first tissue anchoring portion, which is used to attach and secure to the device soft tissue. The soft tissue anchoring portion 2 may be formed in a similar manner to those of the other embodiments of the present invention previously described such that it includes a support plate 8 having an exposed surface from which outwardly extends a plurality of angled barbs 10, the barbs 10 preferably extending from the surface of the support plate at an angle of preferably between about 30 degrees and about 60 degrees, and more preferably at about 45 degrees. The elongated mesh strip 20 which serves as the connection means may pass through a bore 16 which extends longitudinally axially through the center of the support plate 8 of the soft tissue anchoring portion 2 and may engage gripping means inside the bore, such as the ratchet teeth 18 described with respect to the earlier embodiment shown in FIGS. 3A-3C, to allow a one-way movement of the mesh connection strip 20 through the soft tissue anchoring portion 2. Of course, other gripping means may be suitable for use with the present invention, such as a pre-tied knot formed in the mesh connection strip 20, a friction locking collar or a crimped-on staple or other means, such as described previously. Alternatively, no gripping means may be included, and the surgeon simply ties off with a knot the end of the mesh connection strip 20 as it passes through the support plate 8 of the soft tissue anchoring portion 2.

Thus, the mesh connection strip 20 could either be extendable or inextendable through the first tissue anchoring portion 2, depending on the desired characteristics of the device and the requirements of the surgeon for the particular surgical application. For example, if the device is made extendable (i.e., adjustable in length), and if the stiffness of the device is tailored to the particular application, such as by using a thicker mesh or a mesh material which is less flexible, the device may be provided with properties that will exert a force on the tissue that will keep the tissue taut as it heals. An additional advantage of the second tissue anchoring portion (i.e., the "Part B" tissue engagement means 4) being formed of a mesh material is that it will allow a much smaller entry profile for the device during surgical implantation, as it may be rolled up during the surgical procedure.

Figure 7:
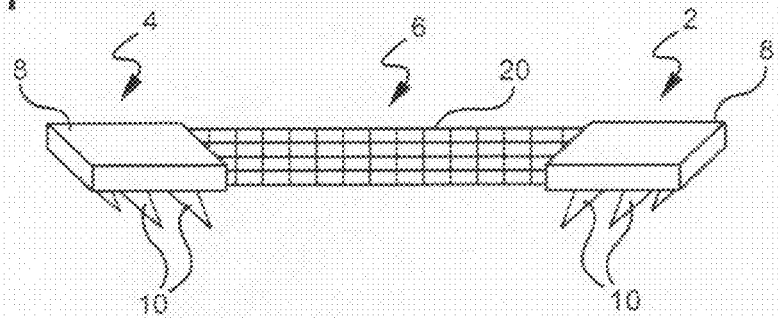
FIG. 7 is a perspective view of a device for attaching, relocating or reinforcing tissue formed in accordance with a sixth form of the present invention.
Figure 8:
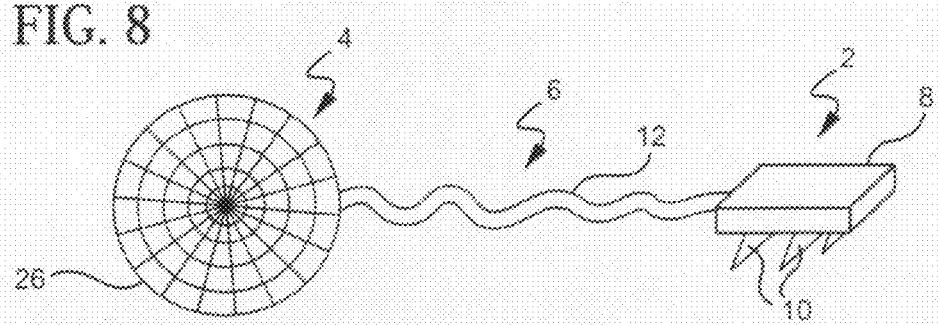
FIG. 8 is a perspective view of a device for attaching, relocating or reinforcing tissue formed in accordance with a seventh form of the present invention.

Alternatively, the device of the present invention may be formed from two barbed anchoring portions (i.e., a "Part A" and "Part B" tissue engagement means 2, 4) interconnected by an elongated mesh strip 20 serving as the "Part C" connection means 6, as shown in FIG. 7 of the drawings. Each of the two barbed anchoring portions 2, 4 preferably includes a support plate 8 having an exposed surface from which a plurality of angularly-disposed barbs 10 outwardly extend. The mesh connection strip 20 may be fixedly joined to and between the support plate 8 of each of the two barbed anchoring portions 2, 4 or, alternatively, may pass through longitudinally axially extending bores 16 formed in one or both of the barbed anchoring portions 2, 4 so that the mesh connection strip 20 can be adjusted with respect to one or both of the anchoring portions 2, 4 in order to adjust the distance between the anchoring portions during the surgical implantation procedure, in the same manner as described previously with respect to the embodiment shown in FIG. 6 of the drawings. Again, gripping means, such as described previously with respect to the embodiment shown in FIG. 6, may be included in one or both of the barbed anchoring portions 2, 4 to permit only uni-directional movement of the mesh connection strip 20 in opposite directions through each respective anchoring portion. The embodiment shown in FIG. 7, having preferably an adjustable mesh connection strip 20 with two barbed anchoring portions 2, 4, could find utility in supporting the soft tissues of the neck.

Another embodiment of the present invention is a variation of that shown in FIG. 6 of the drawings. In particular, this embodiment includes a barbed anchoring portion, defining a "Part A" soft tissue engagement means 2, at one end of the device, a section of mesh material 26, such as the "spider web" configured structure of the embodiment shown in FIG. 6, as the second tissue anchoring portion (i.e., a "Part B" tissue engagement means 4), and a suture 12 interposed between and interconnecting the two tissue anchoring portions 2, 4. The soft tissue anchoring portion 2, again, may be formed with a support plate 8 having an exposed surface from which angularly extend a plurality of barbs 10 to engage the soft tissue of the patient and may include a longitudinally axially extending bore 16 through which the suture 12 passes, and gripping means, such as ratchet teeth 18 internal to the bore, such as described with respect to the embodiments shown in FIGS. 3A-3C to allow the distance between the anchoring portions 2, 4 to be adjusted by the surgeon pulling on the end of the suture 12 which passes through the soft tissue anchoring portion 2 of the device, with only one-way directional movement being permitted by the gripping means so that the suture 12, defining the connection means 6, does not loosen and the selected distance between the two anchoring portions 2, 4 does not change after the surgical procedure has been completed. Again, other gripping means, such as described previously in the other embodiments, may be used in the device of the present invention shown in FIG. 7. Alternatively, no gripping means need be included, and the surgeon simply ties a knot in the end of the suture 12 which passes through the soft tissue anchoring portion 2 to prevent the suture 12 from slipping back through the bore 16 of the anchoring portion 2. This embodiment of the present invention shown in FIG. 7 is particularly useful in facial plastic surgery, because the profile of the connection element 6 is kept to a minimum and, therefore, the damage that needs to be done to implant the device is minimized.

Another adjustable embodiment of the present invention is shown in FIGS. 9 and 9A of the drawings. Here, two barbed anchoring portions (i.e., a "Part A" and "Part B" tissue engagement means 2, 4), each preferably having a support plate 8 with an exposed surface from which outwardly and angularly extends a plurality of barbs 10 to engage the tissue of the patient, are connected with a ratcheting connection element (i.e., the "Part C" connection means 6). More specifically, either one of the two barbed anchoring portions (as shown in FIG. 9, for example, the "Part A" soft tissue engagement means 2) may be fixedly joined to the connection element, and the other of the barbed anchoring portions (as shown in FIG. 9, for example, the "Part B" tissue engagement means 4) may be adjustably joined to the connection element 6. Even more specifically, the "Part B" tissue engagement means 4 preferably includes a support plate 8 having a plurality of barbs 10 extending angularly and outwardly from an exposed surface thereof, and a slot 28 formed longitudinally axially therethrough for receiving the ratcheting connection element 6, as shown in FIG. 9A. Extending at least partially into the slot 28 formed in the tissue anchoring portion 4 is a resilient pawl 30.

The connection element 6 is preferably formed as a flexible or semi-flexible elongated thin strip of material having opposite lateral edges 32 on at least one of which is formed a plurality of ratchet teeth 34. As shown in FIG. 9A, the ratchet teeth 34 of the connection element 6 engages the resilient pawl 30 of the tissue anchoring portion 4 to allow the distance between the two barbed anchoring portions 2, 4 to be adjusted by the surgeon pulling on the end of the connection element 6 which passes through the axial slot 28 of the tissue anchoring portion 4. The engagement of the pawl 30 with the ratchet teeth 34 permits only uni-directional movement of the connection element 6 through the tissue anchoring portion 4 to prevent slippage of the connection element in an opposite direction so that the distance between the two tissue anchoring portions 2, 4 does not change after being adjusted by the surgeon to obtain the desired results. This avoids the need for the surgeon to tie knots in a suture when performing a tissue relocation procedure.

FIG. 10 shows another embodiment of a device formed in accordance with the present invention for attaching, relocating or reinforcing tissue. In this particular embodiment, the connecting element (the "Part C" connection means 6) may be formed as a mesh 36 or from a mesh material that has multiple arms 38 extending in different directions. As shown in FIG. 10, the mesh connecting element 36 has three arms 38 extending in three different directions to define a triangular web for supporting tissue, although it is envisioned to be within the scope of the present invention to provide a connecting element 36 that extends in more directions and having more arms 38 than that shown in FIG. 10. Each of the arms 38 of the mesh connecting element 36 is connected to a respective anchoring portion 40 of the device, either a "Part A" tissue engagement means 2 or a "Part B" tissue engagement means 4. Also, each of the arms 38 may be adjustably connected to one of the tissue anchoring portions 40 so that appropriate tension is provided to the tissue supported by the mesh connecting element 36. The tissue anchoring portions 40 may be in the form of the barbed anchors previously described with respect to several other embodiments of the present invention, for example, one or the other of the tissue anchoring portions 2, 4 shown in FIGS. 3A-3C, FIG. 6 or FIG. 7. More specifically, each of the tissue anchoring portions 40 may include a support plate 8 having an exposed surface from which angularly outwardly extend a plurality of barbs 10, such as described previously, with the support plate 8 having formed longitudinally axially therethrough a bore 16. The arms 38 of the connecting element 36 themselves may pass directly through the axial bores 16 of the support plates 10 of the tissue anchoring portions 40, or they may be connected to sutures 12 which pass through the bores 16 of the support plates 10. Again, like the other embodiments, the tissue anchoring portions 40 may include gripping means, such as ratchet teeth 18, formed in the axial bore 16 of their respective support plates 40 to allow one-way adjustment of the mesh connecting element 36 and to prevent slippage thereof through the tissue anchoring portions. Or, alternatively, one or more of the arms 38 of the mesh connecting element 36 may be fixedly joined to a respective tissue anchoring portion 40 of the device.

Figure 13:
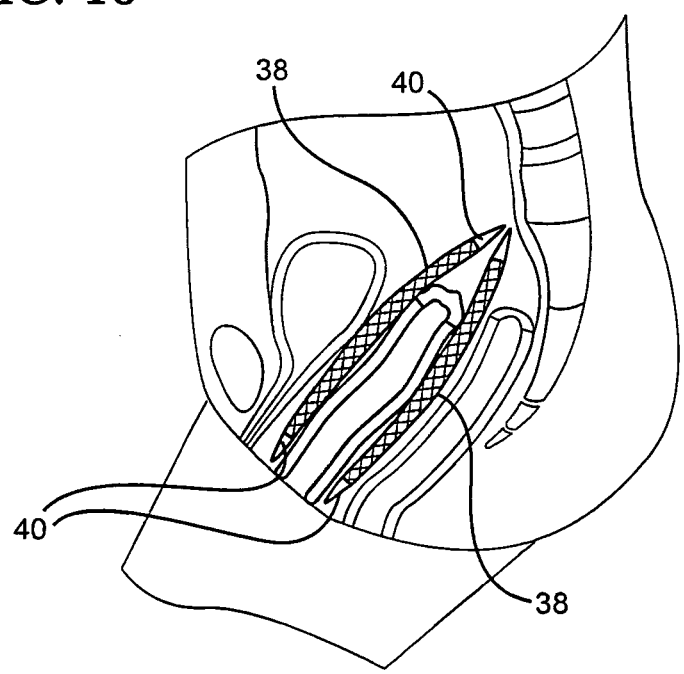
FIG. 13 is a cross-sectional view of a pictorial illustration of the device of the present invention shown in FIG. 10 being implanted in a patient to support the patient's vagina in pelvic organ prolapse repair.

The embodiment shown in FIG. 10 and described previously is particularly useful in supporting large structures, like the breast, during breast reduction surgery, or the vaginal vault during pelvic floor repair. In this latter case, two of the arms 38 would be placed anterior and posterior to the vagina, in the space between the vagina and the urethra and the space between the vagina and the rectum respectively. The remaining arm 38 would then be placed deep in the patient's body, to be anchored to the periosteum near the sacrum. More specifically, FIG. 13 illustrates the location of the device having a mesh connection element 36 with multiple arms 38 implanted in a patient to provide support to the vagina in pelvic organ prolapse repair. More specifically, FIG. 13 shows the preferred deployment of the embodiment of FIG. 10, with the mesh 36 placed anterior and posterior to the vagina through a transvaginal incision or through an endoscopic approach, with the anchors 40 set near the entroitus and into the sacrospinus ligament or the periosteum near the sacrum. The arms 38 of the mesh connecting element 36 are then adjusted by the surgeon to provide the appropriate placement of the vaginal vault.

Figure 12:
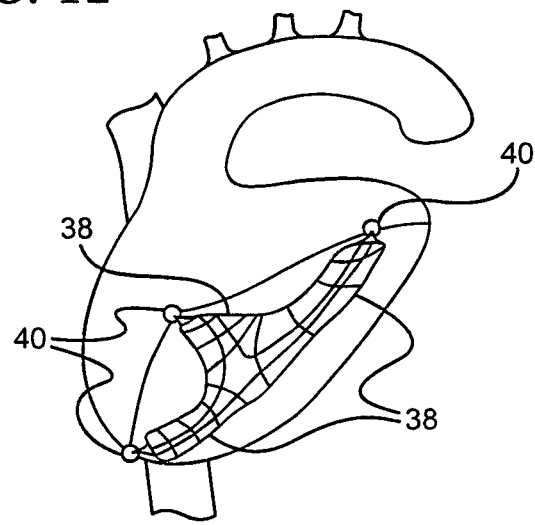
FIG. 12 is a cross-sectional view of a pictorial illustration of the device of the present invention shown in FIG. 10 being implanted in a patient's heart to provide support for patients experiencing dilated congestive heart failure.

The embodiment of the present invention shown in FIG. 10 is also suitable for use for patients with congestive heart failure. In this situation, and as illustrated by FIG. 12 of the drawings, one tissue anchoring portion 40 of the device would be placed at the apex of the heart, on the anterior surface, and the other two tissue anchoring portions 40 would be placed in the a trio-ventricular septum, as shown in FIG. 12. The surgeon would then adjust the mesh connecting element 36 with respect to the anchoring portions 40 until the appropriate level of ventricular volume change is achieved.

Primarily, throughout this disclosure of the present invention, tissue anchoring portions of the device of the present invention, in the various embodiments, have been described as having support plates 8 with angular barbs 10 extending therefrom, in order to facilitate an understanding of the present invention and to describe one form of tissue engagement means which is suitable for use. However, it is envisioned to be within the scope of the present invention to have tissue anchoring portions of the device formed with other structure that is capable of attaching to either soft or hard tissue. FIGS. 11A-11E show other forms of tissue engagement means 2, 4, either of the "Part A" or "Part B" type, that are suitable for use with the device of the present invention and are envisioned to be within the scope of the present invention.

Figure 11A:
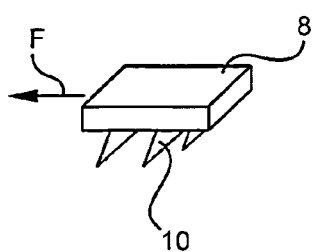
FIG. 11A is a perspective view of a first form of a tissue engagement means of a device for attaching, relocating or reinforcing tissue formed in accordance with the present invention.

More specifically, FIG. 11A shows the tissue anchoring portion having a support plate 8 with angularly disposed barbs 10 extending from an exposed surface thereof, such as described previously with respect to many of the embodiments shown in the figures. These barbs 10 are shown to extend in the direction of the force applied, such as when the connecting element is tightened. The arrow F shown in FIG. 11A denotes the direction of the force applied against the tissue anchoring portion, and the angle of the barbs 10 extending therefrom resists such force.

Figure 11B:
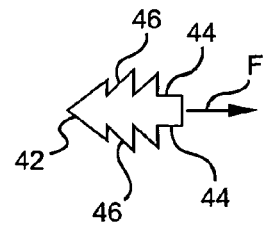
FIG. 11B is a perspective view of a second form of a tissue engagement means of a device for attaching, relocating or reinforcing tissue formed in accordance with the present invention.

FIG. 11B shows an alternative form of a tissue anchoring portion, either of the "Part A" formed as a plate-like structure 42 which can be said to be tree-shaped in plan view, having opposite lateral edges 44 with a plurality of barbs 46 extending outwardly from each lateral edge 44. Unlike the "out of plane" barbs 10 of the tissue anchoring portion shown in FIG. 11A, the tissue anchoring portion of FIG. 11B has "in plane" barbs 46. The barbs 46 extend angularly from the lateral edges 44 in a direction toward the force F applied against the tissue anchoring portion to oppose such force exerted by the connecting element 6 joined to the tissue anchoring portion of the device.

Figure 11C:
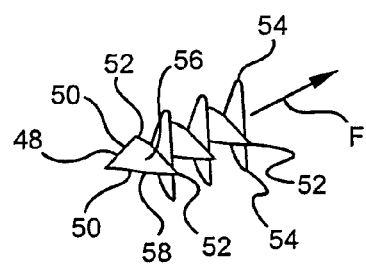
FIG. 11C is a perspective view of a third form of a tissue engagement means of a device for attaching, relocating or reinforcing tissue formed in accordance with the present invention.

Alternatively, the tissue anchoring portion of the device may include "in plane" and "out of plane" barbs, such as shown in FIG. 11C. More specifically, a thin, flat planar member 48 having opposite lateral edges 50, with barbs 52 extending angularly outwardly from the lateral edges 50, as in the embodiment shown in FIG. 11B, may further have angularly protruding barbs 54 extending outwardly from the opposite top and bottom sides 56, 58 of the planar member 48. Again, the barbs 52 formed on the lateral edges 50 and the barbs 54 formed on the top and bottom sides 56, 58 are angularly disposed in the direction of the force F applied against the tissue anchoring portion in order to oppose such force.

Figure 11D:
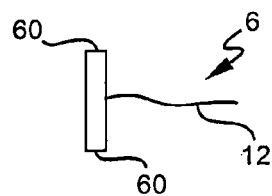
FIG. 11D is a perspective view of a fourth form of a tissue engagement means of a device for attaching, relocating or reinforcing tissue formed in accordance with the present invention.
Figure 11E:
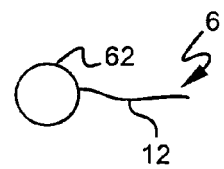
FIG. 11E is a perspective view of a fifth form of a tissue engagement means of a device for attaching, relocating or reinforcing tissue formed in accordance with the present invention.

It is further contemplated that the tissue anchoring portions of the device could be T-shaped, such as shown in FIG. 11D, with outwardly extending legs 60 joined to the connection element 6 which may be a suture or mesh or take on another form. Again, alternatively, the tissue anchoring portion may be in the form of a large bead or sphere 62 at the end of the connection means 6, such as shown in FIG. 11E, that prevents the tissue anchoring portion of the device from pulling through the tissue to which it is attached.

Alternatively, the tissue anchoring portions 2, 4 of the device may be sewn in place, glued in place with a biocompatible adhesive, such as a fibrin glue, or implanted and fixed in position through the ingrowth of tissue. It is also possible to make the mesh connective element (the "Part C" connection means 6), such as that shown in FIG. 9 of the drawings, self-adhesive by coating it with fibrin or thrombin and allowing it to "clot" into place.

Furthermore, the tissue anchoring portions 2, 4 of the device of the present invention may be made out of a variety of materials, including resorbable plastics like PLA (poly lactic acid), PGA (poly glycolic acid) and polydioxanone, or non-resorbable plastics, such as nylon, polyester and others. The tissue anchoring portions 2, 4, either one or both of the "Part A" or "Part B" type, may also be formed from a resorbable metal, such as magnesium, or permanent metals, such as stainless steel and nickel-titanium alloys.

The connecting element (i.e., the "Part C" connection means 6) which is interposed between the two tissue anchoring portions 2, 4 may be formed from sutures, a mesh, molded strips or metal. The materials of the connecting element could be selected to be resorbable, such as PLA, PGA, magnesium and others, or non-resorbable, such as stainless steel, nickel-titanium, titanium and others.

Various applications of the device of the present invention for attaching, relocating or reinforcing tissue have been described herein. However, it should be understood that the invention is useful in a variety of procedures where the suspension or reattachment of soft tissue is required. These procedures include "facelift" procedures, particularly for the upper and midface, and other facial cosmetic surgery, such as neck and jowl lifts. The device of the present invention could also be used to provide support in breast surgery (e.g., breast lift or mastopexy), testicular lift procedures and repair of inguinal hernias. The device of the present invention may also be used to provide support to incompetent venous valves in patients suffering from varicose veins by wrapping the vein in the area of the valve and reshaping the valve until it closes appropriately.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A device for attaching, relocating or reinforcing tissue, which comprises:
   at least two tissue engagement means, including a first tissue engagement means having a first plate with a major face and a plurality of first barbs projecting from the major face and a second tissue engagement means having a second plate with a first major face, a second major face, and a plurality of second barbs projecting from one of the first and second major faces of the second plate; and
   a suture interposed between and interconnecting the first tissue engagement means and the second tissue engagement means, wherein the second plate of the second tissue engagement means has an axial bore extending between the first and second major faces of the second plate and along the length of the second plate and gripping means extending into the axial bore for engaging the suture to allow movement of the suture with respect to the second plate in a first direction only and to prevent movement of the suture with respect to the second plate in a second direction that is opposite the first direction; and wherein the suture has a first end that is fixedly joined to the first plate and a second free end that is slidable in the first direction through the axial bore of the second plate.

2. A device for attaching, relocating or reinforcing tissue as defined by claim 1, wherein the suture is adapted to slide past the gripping means in the first direction to allow the distance between the first tissue engagement means and the second tissue engagement means to be adjusted and the gripping means exert a force on the suture to prevent the movement of the suture in the second direction that is opposite the first direction.

3. A device for attaching, relocating or reinforcing tissue as defined by claim 2, wherein the gripping means comprise a plurality of ratchet teeth disposed within the axial bore, and wherein the plurality of ratchet teeth are spaced from one another along the length of the second plate.

4. A device for attaching, relocating or reinforcing tissue as defined by claim 3, wherein the ratchet teeth extend from diametrically opposite sides of the axial bore and radially into the axial bore to closely engage the suture, and wherein the ratchet teeth on one side of the axial bore are in mirrored symmetry to the ratchet teeth on the other side of the axial bore.

5. A device for attaching, relocating or reinforcing tissue as defined by claim 4, wherein the ratchet teeth are angled away from the first plate to allow the suture to slip past the ratchet teeth in the first direction while preventing movement of the suture through the axial bore in the second direction.

6. A device for attaching, relocating or reinforcing tissue as defined by claim 1, wherein the first and second barbs extend angularly outwardly from the major faces.

7. A device for attaching, relocating or reinforcing tissue as defined by claim 6, wherein the barbs extend at an angle of between about 30 degrees and about 60 degrees.

8. A device for attaching, relocating or reinforcing tissue as defined by claim 6, wherein the barbs extend at an angle of about 45 degrees thereto.

9. A device for attaching, relocating or reinforcing tissue as defined by claim 1, wherein the gripping means includes ratchet teeth extending from diametrically opposite sides of the axial bore for engaging the suture to allow for the movement of the suture with respect to the second plate in the first direction only and to prevent movement of the suture with respect to the second plate in the second direction that is opposite the first direction.

10. A device for attaching, relocating or reinforcing tissue as defined by claim 1, wherein the barbs on the first plate are longer than the barbs on the second plate.

11. A device for attaching, relocating or reinforcing tissue as defined by claim 1, wherein the second plate has a first end and a second end defining the length of the second plate, and wherein the axial bore extends the length of the second plate from the first end to the second end of the second plate.

12. A device for attaching, relocating or reinforcing tissue, which comprises:
- a first tissue anchor having a first plate with a major face and a plurality of first barbs projecting from the major face of the first plate;
- a second tissue anchor having a second plate with a first major face, a second major face, and a plurality of second barbs projecting from one of the first and second major faces of the second plate;
- an axial bore extending through the second plate between the first and second major faces of the second plate and along the length of the second plate;
- the second plate having a gripping structure extending into the axial bore;
- a suture having a first end fixedly joined to the first plate and a second free end passable through the axial bore extending through the second plate, wherein the gripping structure provided in the axial bore allows the suture to move through the axial bore in a first direction only while preventing movement of the suture through the axial bore in a second direction that is opposite the first direction.

13. A device for attaching, relocating or reinforcing tissue as defined by claim 12, wherein the gripping structure comprises ratchet teeth extending from opposite sides of the axial bore.

14. A device for attaching, relocating or reinforcing tissue as defined by claim 13, wherein the ratchet teeth are angled away from the first tissue anchor.

15. A device for attaching, relocating or reinforcing tissue as defined by claim 12, wherein the first plate is larger than the second plate, and wherein the first barbs are longer than the second barbs.

16. A device for attaching, relocating or reinforcing tissue as defined by claim 12, further comprising:
- a second axial bore extending through the second plate between the first and second major faces of the second plate and along the length of the second plate, the second axial bore being parallel to the first axial bore;
- the second plate having a second gripping structure extending into the second axial bore;
- a second suture having a first end fixedly joined to the first plate and a second free end adapted to pass through the second axial bore in the second plate, wherein the second gripping structure provided in the second axial bore allows the second suture to move through the second axial bore in the first direction only while preventing movement of the suture through the second axial bore in the second direction that is opposite to the first direction.

17. A device for attaching, relocating or reinforcing tissue as defined by claim 12, wherein the second plate has a first end and a second end defining the length of the second plate, wherein the axial bore extends the length of the second plate from the first end to the second end of the second plate, wherein the gripping means comprise a plurality of ratchet teeth disposed within the axial bore, and wherein the plurality of ratchet teeth disposed within the axial bore are spaced from one another along the length of the second plate.

18. A device for attaching, relocating or reinforcing tissue, which comprises:
- a first tissue anchor having a first plate with a major face and a plurality of first barbs projecting from the major face;
- a second tissue anchor having a second plate with a first major face, a second major face, and a plurality of second barbs projecting from one of the first and second major faces of the second plate, wherein the first plate is larger than the second plate and the first barbs on the first plate are longer than the second barbs on the second plate;
- an axial bore extending through the second plate between the first and second major faces of the second plate and along the length of the second plate;
- the second plate having ratchet teeth extending from diametrically opposed sides of the axial bore;
- a suture having a first end fixedly joined to the first plate and a second free end passable through the axial bore in the second plate, wherein the ratchet teeth engage the suture for allowing the suture to move through the axial bore in a first direction only while preventing movement of the suture through the axial bore in a second direction that is opposite the first direction.

19. A device for attaching, relocating or reinforcing tissue as defined by claim 18, further comprising:
- a second axial bore extending through the second plate between the first and second major faces of the second plate and along the length of the second plate, the second axial bore being parallel to the first axial bore;
- the second plate having second ratchet teeth extending from diametrically opposite sides of the second axial bore;
- a second suture having a first end fixedly joined to the first plate and a second free end passable through the second axial bore in the second plate, wherein the second ratchet teeth engage the second suture for allowing the second suture to move through the second axial bore in the first direction only while preventing movement of the second suture through the second axial bore in the second direction that is opposite the first direction.

* * * * *